US007762252B2

(12) United States Patent
Prete

(10) Patent No.: US 7,762,252 B2
(45) Date of Patent: Jul. 27, 2010

(54) DEVICES, SYSTEMS AND METHODS FOR OPERATION OF BREATHING APPARATUSES IN MULTIPLE MODES

(75) Inventor: Christopher L. Prete, Cranberry Township, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 845 days.

(21) Appl. No.: 11/594,380

(22) Filed: Nov. 8, 2006

(65) Prior Publication Data

US 2007/0251525 A1 Nov. 1, 2007

(51) Int. Cl.
*A61M 16/00* (2006.01)
*A62B 7/00* (2006.01)
*A62B 9/02* (2006.01)

(52) U.S. Cl. ............................ 128/204.18; 128/205.24

(58) Field of Classification Search ............................... 128/201.22–201.25, 203.12–203.14, 204.18, 128/204.21–204.23, 204.26, 205.18, 205.22, 128/205.24
See application file for complete search history.

(56) References Cited

U.S. PATENT DOCUMENTS 2,391,877 A * 1/1946 Cahan ........................ 137/102
5,222,490 A * 6/1993 Pomerantz et al. ..... 128/204.26
2002/0162553 A1* 11/2002 Hamilton et al. ....... 128/204.18

FOREIGN PATENT DOCUMENTS

| | | |
|---|---|---|
| DE | 2853225 | 6/1980 |
| DE | 19503027 | 3/1996 |
| FR | 1476589 | 4/1967 |
| GB | 2264646 | 9/1993 |
| JP | 2003062096 | 3/2003 |

* cited by examiner

*Primary Examiner*—Justine R Yu
*Assistant Examiner*—Kristen C Matter
(74) *Attorney, Agent, or Firm*—Henry E. Bartony, Jr.; James G. Uber

(57) ABSTRACT

A breathing system with a facepiece that includes a first port adapted to be placed in fluid connection with the outlet of a regulator assembly to introduce pressurized breathing gas into the facepiece; a second port adapted to be connected to an air purifying system; and an exhaust valve through which the user's exhausted breath can exit the facepiece. The breathing system also includes a pressure adjustment mechanism that includes a communication link in communicative connection with an actuator such that the exhaust pressure adjustment mechanism sets the internal facepiece pressure required to open the exhaust valve, independently of the respiration of the user, to a first pressure when the actuator is in the first state, to a second pressure when the actuator is in the second state. The first pressure is higher than the second pressure.

16 Claims, 9 Drawing Sheets

DEVICES, SYSTEMS AND METHODS FOR OPERATION OF BREATHING APPARATUSES IN MULTIPLE MODES

BACKGROUND OF THE INVENTION

The present invention relates generally to devices, systems and methods for the operation of breathing apparatuses in multiple modes and, particularly, to devices, systems and methods for operating a breathing apparatus with different pressures with a facepiece in different modes of operation.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein are incorporated by reference.

A self contained breathing apparatus ("SCBA") is a device used to enable breathing in environments which are immediately dangerous to life and health (IDLH). For example, firefighters wear an SCBA when fighting a fire. The SCBA typically has a harness supporting an air tank which is connected to a facepiece, all of which are worn or carried by the user. The tank typically contains air or gas under high pressure (2200 psi-4500 psi) and is connected to a first stage regulator which reduces the pressure to about 80 psi. The SCBA usually has a second stage regulator that has an inlet valve which controls the flow of air for breathing between the air tank and the facepiece. Typically, the inlet valve controls the flow of air through the second state regulator in response to the respiration of the user. Such respiration-controlled regulator assemblies are disclosed, for example, in U.S. Pat. Nos. 4,821,767 and 5,016,627.

Typically, a diaphragm divides the regulator assembly into an inner chamber having a pressure corresponding to the pressure within the facepiece of the SCBA and an outer chamber having a pressure corresponding to the pressure in the surrounding environment, which is typically ambient pressure. The diaphragm is coupled to an actuating mechanism which opens and closes the inlet valve. The user's respiration creates a pressure differential between the inner and outer chambers of the regulator assembly which, in turn, causes displacement of the diaphragm thereby controlling (that is, opening and closing) the inlet valve mechanism. As a result, such regulators are often called pressure demand regulators.

The facepiece of the SCBA is typically maintained at a positive pressure as compared to the surrounding environmental pressure to, for example, prevent toxic gases and vapors in the surrounding environment from entering the facepiece. This positive pressure can, for example, be facilitated by biasing the diaphragm with a spring.

Combination breathing apparatuses are devices that combine two or more types of National Institute for Occupational Safety and Health (NIOSH) approved breathing apparatuses into a single integrated system. A currently available example of a combination breathing apparatus is the dual-purpose FIREHAWK® SCBA available from Mine Safety Appliances Company of Pittsburgh, Pa. That device integrates an SCBA and an airline respirator. Another example of a combination device is the DUO-FLO® apparatus, available from Mine Safety Appliances Company, which combines an airline respirator and a gas mask (a type of air purifying respirator). A combination SCBA and PAPR is described in U.S. Patent Application Publication No. US 2004/0182395 published Sep. 23, 2004 and U.S. Patent Application Publication No. US 2005/0022817 published Feb. 3, 2005.

To meet NIOSH requirements, the exhalation valve for powered air purifying respirators (PAPRs) and air purifying respirators (APRs) must meet low inhalation resistance requirements of 20 mm of water at 85 lpm (liters per minute) flow. That result is typically achieved by using a simple rubber check valve in the exhaust valve. However, use of a simple rubber check valve cannot enable the facepiece to hold air pressure above ambient pressure. The exhalation valve for a pressure demand respirator such as an SCBA or an airline respirator normally includes a rigid valve umbrella with a spring that biases the valve against a valve seat. Use of a biased valve umbrella enables air pressure above ambient to be held in the facepiece at all times, which is a NIOSH requirement for pressure demand respirator. Combining an APR and/or a PAPR with an SCBA or airline respirator, while meeting all NIOSH breathing test requirements, requires that the exhalation valve meet the low resistance requirement of APR and PAPR exhalation resistance and also allowing pressure within the facepiece to be higher than ambient pressure for SCBA or airline pressure demand operation.

Several attempts have been made to provide for switching between respiration modes in breathing apparatuses. For example, United Kingdom Patent Application No. GB 2,264,646 discloses a breathing apparatus including a connector 10 of a pressurized air connection that moves a piston rearward within a fitting 15. A connected cable passing through a sleeve 18 causes a piston to move and change the length of a spring loading an exhalation valve of the breathing apparatus, thereby changing the load on the exhalation valve. Two actions are required to switch respirator modes. First, the user must disconnect the supply line which "turns-off" the air regulator. Second, the user must push the hose end fitting or connector 10 into the facepiece receptacle which switches the exhalation valve from a "pressure demand" mode to a "demand" mode. The user must also disconnect the pneumatic supply line from the air supply and reconnect the supply line to a parking position in the facemask. The disconnection of the supply line can introduce contamination into the hose fittings if done in a contaminated atmosphere. There is also the possibility that the user of the breathing apparatus of GB 2,264,646 will be subjected to high exhalation resistance while in demand mode if the user fails to park the supply line into the receptacle upon removing it from the pressure source or if the air supply runs-out.

European Patent No. EP 0 667 171 discloses a breathing apparatus in which mechanical abutment of an abutment member on a connection for an air pressure connection causes a pin to move to cause a first spring to place force on the diaphragm. In the case of the attachment of a filter or a vacuum rather than the pressurized air connection, there is no similar abutment member to contact the pin. In the case of attachment of a filter or a vacuum, a second spring exerts force on the diaphragm with less force than the first spring. The user of the breathing apparatus of European Patent No. EP 0 667 171 must be in a clean environment to switch exhalation valve modes as such a switch requires removing the air purifying or air supplying device from the admitting duct.

Italian Patent No. IT 1,227,248 apparently discloses a breathing apparatus (see, for example, FIG. 1) in which pressure is used to inflate a bellows to change force exerted upon a diaphragm of an exhalation valve via an exhalation valve spring. The pressure is apparently provided by the low pressure air supplied by a second stage regulator or "demand valve". Providing pressure from the second stage regulator results in expansion and contraction of the bellows as the user breathes, potentially causing the exhalation valve spring to change compression and thereby changing the pressure required to open the exhalation valve as the user inhales and exhales.

It remains desirable to develop improved devices, systems and methods for operating (and preferably automatically operating) a breathing apparatus with different pressures within a facepiece in different modes of operation wherein the pressure within the facepiece is different depending upon the mode of operation.

SUMMARY OF THE INVENTION

In one aspect, the present invention provides a breathing system including a source of pressurized breathing gas and a regulator assembly including a valve assembly, an inlet for connection to a source of pressurized breathing gas, an outlet to provide breathing gas to a user and a valve assembly actuator for controlling the flow of breathing gas between the inlet and the outlet via the valve assembly based at least in part on the respiration of the user. The breathing system also includes an actuator via which flow of pressurized breathing gas from the source of pressurized breathing gas to the inlet of the regulator assembly is started when the actuator is placed in a first state and is stopped when the actuator is placed in a second state. A facepiece of the breathing system includes a first port adapted to be placed in fluid connection with the outlet of the regulator assembly to introduce pressurized breathing gas into the facepiece, a second port adapted to be connected to an air purifying system; and an exhaust valve through which the user's exhausted breath can exit the facepiece. The breathing system also includes a pressure adjustment mechanism in operative connection with the exhaust valve and operable to adjust the internal facepiece pressure required to open the exhaust valve. The pressure adjustment mechanism includes a communication link in communicative connection with the actuator such that the exhaust pressure adjustment mechanism sets the internal facepiece pressure required to open the exhaust valve independent of respiration of the user to a first pressure when the actuator is in the first state, and the exhaust pressure adjustment mechanism sets the internal facepiece pressure required to open the exhaust valve to a second pressure when the actuator is in the second state. The first pressure is higher than the second pressure.

The communication link of the pressure adjustment mechanism can, for example, include a wireless communication link, a wired communication link, a mechanical communication link or a pneumatic communication link.

In one embodiment, the exhaust valve includes a valve closure member and a valve seating over which the valve closure member is seated to close the exhaust valve. The pressure adjustment mechanism can include a force applicating element to place a first force on the valve closure member when the actuator is in the first state and to place a second force on the valve closure member when the actuator is in the second state. The first force is greater than the second force. The force applicating element can, for example, include a spring. The working length of the spring can, for example, be adjusted to a first working length by the pressure adjustment mechanism when the actuator is in the first state, and the working length of the spring can be adjusted to a second working length by the pressure adjustment mechanism when the actuator is in the second state. The first working length is shorter than the second working length.

In one embodiment, the communication link of the pressure adjustment mechanism includes a pneumatic fluid path providing fluid connection of pressurized breathing gas prior to reduction of pressure of the pressurized breathing gas in the regulator assembly to the pressure adjustment mechanism when the actuator is in the first state and preventing fluid connection of pressurized breathing gas to the pressure adjustment mechanism when the actuator is in the second state.

The pressure adjustment mechanism can further include a piston chamber having a piston slidably disposed therein. In the case that the force applicating member is a spring, the spring can be in operative connection with the piston. The pneumatic fluid path can, for example, provide fluid connection between the piston chamber and the regulator assembly inlet such that the piston is placed in a first position in which it compresses the spring to the first working length when the actuator is in the first state. The piston is placed in a second position in which the piston allows the spring to relax to the second working length when the actuator is in the second state. The piston can be biased in the second position such that the piston returns to the second position when the actuator is in the second state. The piston can, for example, be biased in the second position by a return spring.

The regulator assembly can include an outlet port in fluid connection with the regulator assembly inlet. The outlet port can be adapted to make a fluid connection with an inlet port in fluid connection with the pneumatic fluid path when the outlet of the regulator assembly is placed in fluid connection with the first port of the facepiece. The outlet port can, for example, include a normally closed valve which is opened when the outlet port makes a fluid connection with the inlet port.

In another aspect, the present invention provides a facepiece for use in a breathing system including a first port adapted to be placed in fluid connection with the outlet of a regulator assembly to introduce pressurized breathing gas into the facepiece from a source of pressurized breathing gas; a second port adapted to be connected to an air purifying system; an exhaust valve through which the user's exhausted breath can exit the facepiece; and a pressure adjustment mechanism in operative connection with the exhaust valve and operable to adjust the internal facepiece pressure required to open the exhaust valve. The pressure adjustment mechanism includes a communication link adapted to be placed in communicative connection with an actuator. The actuator controls flow of pressurized breathing gas from the source of pressurized breathing gas to the regulator assembly such that flow is started when the actuator is placed in a first state and flow is stopped when the actuator is placed in a second state. The pressure adjustment mechanism sets the internal facepiece pressure required to open the exhaust valve independent of respiration of the user to a first pressure when the actuator is in the first state. The exhaust pressure adjustment mechanism sets the internal facepiece pressure required to open the exhaust valve to a second pressure when the actuator is in second state, the first pressure being higher than the second pressure.

The exhaust valve can, for example, include a valve closure member and a valve seating over which the valve closure member is seated to close the exhaust valve. The pressure adjustment mechanism can include a force applicating element to place a first force on the valve closure member when the actuator is in the first state and a second force on the valve closure member when the actuator is in the second state, the first force being greater than the second force. As discussed above, the force applicating element can include a spring. In one embodiment, the working length of the spring is adjusted to a first working length by the pressure adjustment mechanism when the actuator is in the first state, and the working length of the spring is adjusted to a second working length by the pressure adjustment mechanism when the actuator is in the second state, the first working length being shorter than the second working length.

The communication link of the pressure adjustment mechanism can, for example, include a pneumatic fluid path providing flow of pressurized breathing gas prior to reduction of pressure of the pressurized breathing gas in the regulator assembly to the pressure adjustment mechanism when the actuator is in the first state and preventing flow of pressurized breathing gas to the pressure adjustment mechanism when the actuator is in the second state.

The pressure adjustment mechanism can further include a piston chamber having a piston slidably disposed therein. The spring of the force applicating element can, for example, be in operative connection with the piston. The pneumatic fluid path can provide fluid connection between the piston chamber and the regulator assembly inlet such that the piston is placed in a first position in which the piston compresses the spring to the first working length when the actuator is in the first state and the piston is placed in the a second position in which the piston allows the spring to relax to the second working length when the actuator is in the second state. The piston can be biased in the second position such that the piston returns to the second position when the actuator is in the second state. The piston can, for example, be biased in the second position by a return spring.

The present invention, along with the attributes and attendant advantages thereof, will best be appreciated and understood in view of the following detailed description taken in conjunction with the accompanying drawings.

DETAILED DESCRIPTION OF THE INVENTION

In the present invention a breathing apparatus such as a self contained breathing apparatus (SCBA) or airline respirator is operable at different pressures within the facepiece during different modes of operation. In a representative embodiment set forth below, a breathing apparatus is described which, for example, is operable in a pressure demand mode as well as in a PAPR and/or APR demand mode. In several representative embodiments described herein, the devices, systems of methods of the present invention allow a user to quickly, simply and automatically (that is, without direct manual intervention) switch between facepiece exhalation modes such as from pressure demand to demand or from demand to pressure demand. For use in the United States, the combination breathing apparatuses of the present invention preferably meet NIOSH performance requirements regardless of the mode of operation (for example, SCBA or airline and PAPR or APR).

In general, the breathing system of the present invention include a pressure adjustment mechanism in operative connection with the exhaust valve and operable to automatically adjust the internal facepiece pressure required to open the exhaust valve. A communication link is provided between the exhaust pressure adjustment mechanism and an actuator (for example, a valve such as an air tank associated with provision of air from the air tank to a first stage regulator) that is operable to pressurize and depressurize the second stage regulator assembly. The pressure adjustment mechanism sets the internal facepiece pressure required to open the exhaust valve to a first pressure when the actuator is in a first (pressurized) state (wherein pressurized breathing gas is supplied to the second stage regulator assembly). The pressure adjustment mechanism sets the internal facepiece pressure required to open the exhaust valve to a second pressure when the actuator is in second (depressurized) state (wherein pressurized breathing gas is not being supplied to the second stage regulator assembly). The first pressure (corresponding to an SCBA or airline pressure demand mode) is higher than the second pressure (corresponding to a demand mode such as in APR or PAPR operation).

Figure 1A:
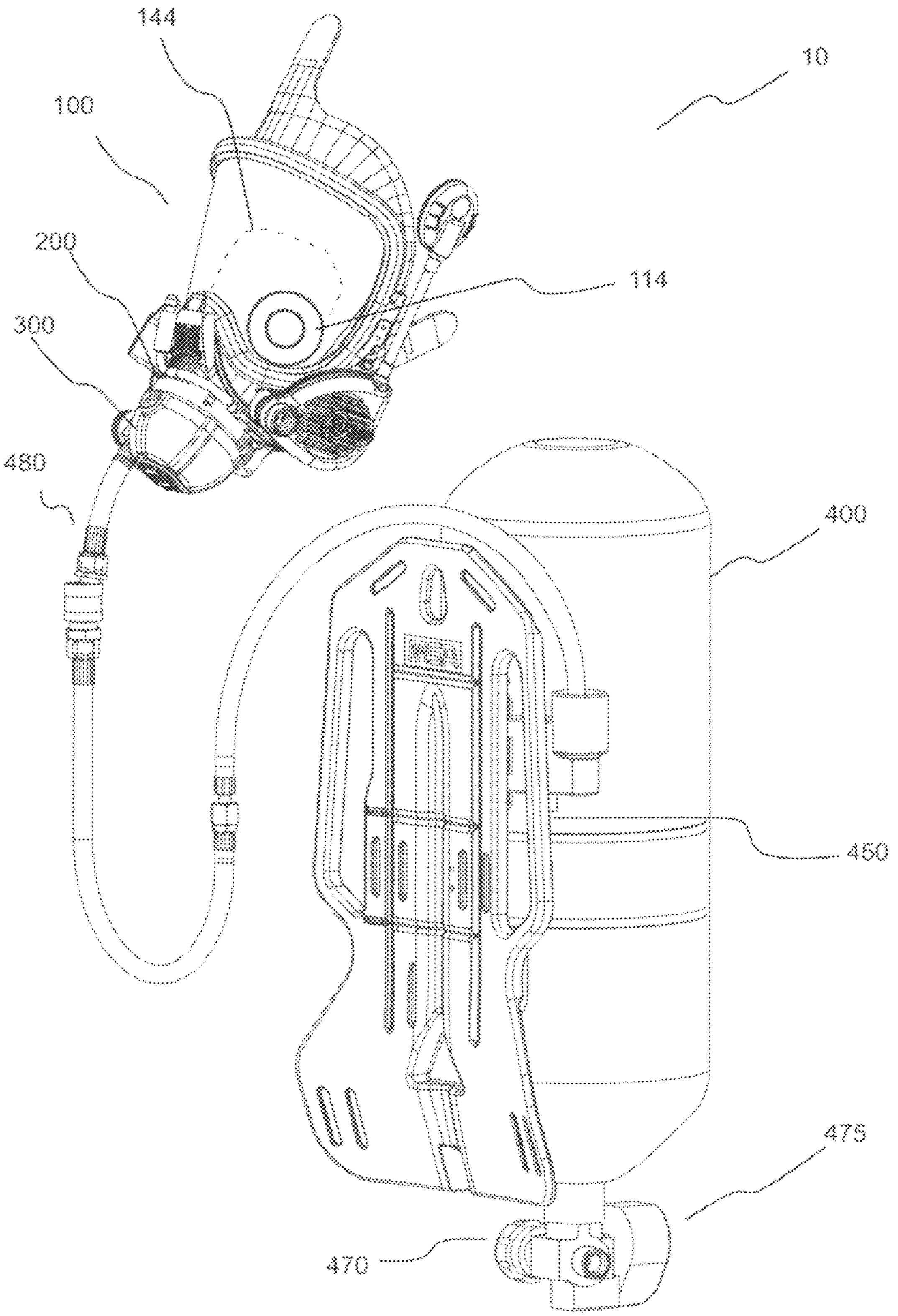
FIG. 1A illustrates a perspective view of an embodiment of a breathing system of the present invention adapted for use in a breathing apparatus (for example, a self contained breathing apparatus) pressure demand mode in which the facepiece is maintained at a pressure above ambient pressure throughout a breathing cycle.
Figure 1B:
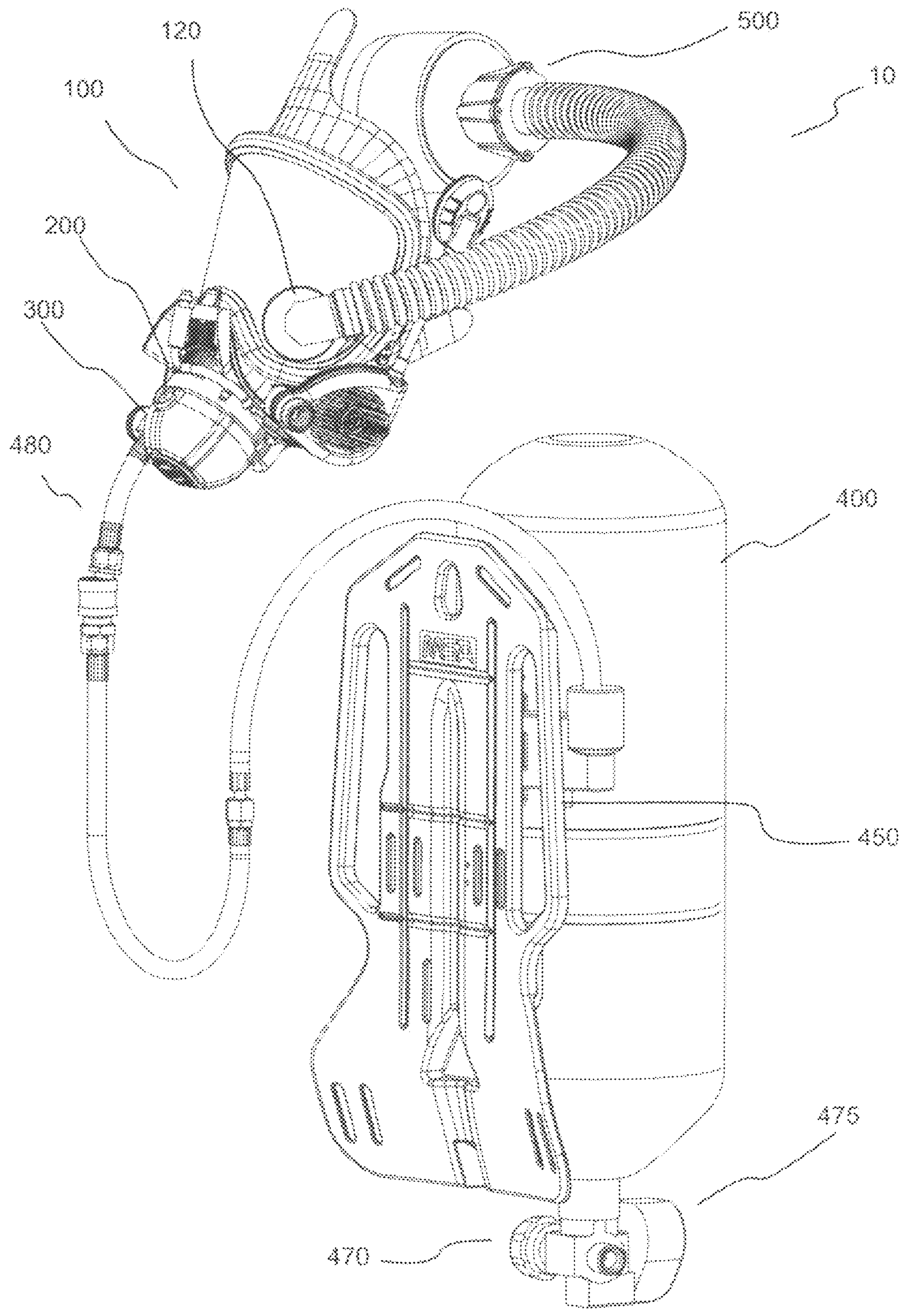
FIG. 1B illustrates a perspective view of the breathing system of FIG. 1A adapted for use in a demand mode with an air purifying system.
Figure 1C:
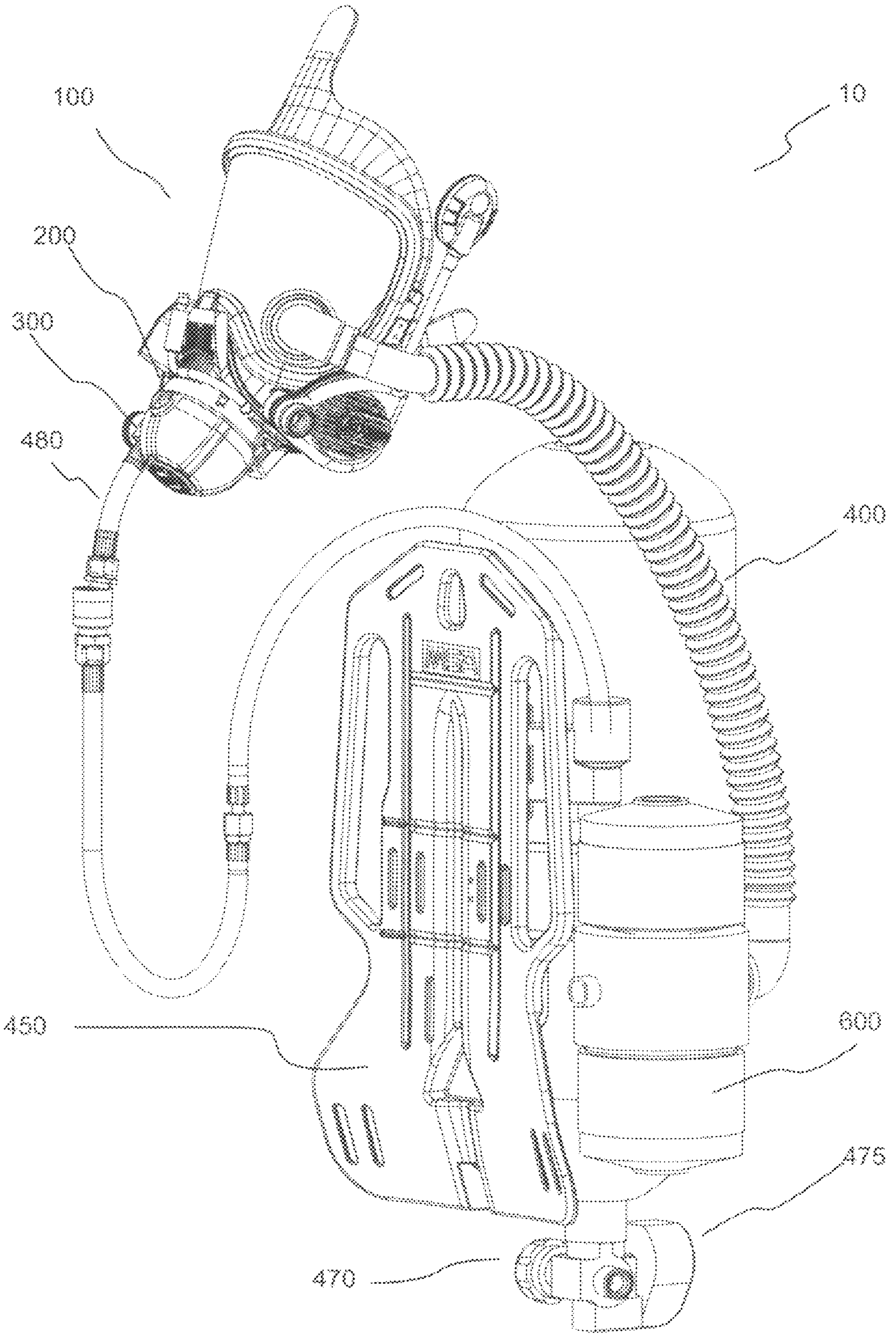
FIG. 1C illustrates a perspective view of the breathing system of FIG. 1A adapted for use in a demand mode with an powered air purifying system.
Figure 2A:
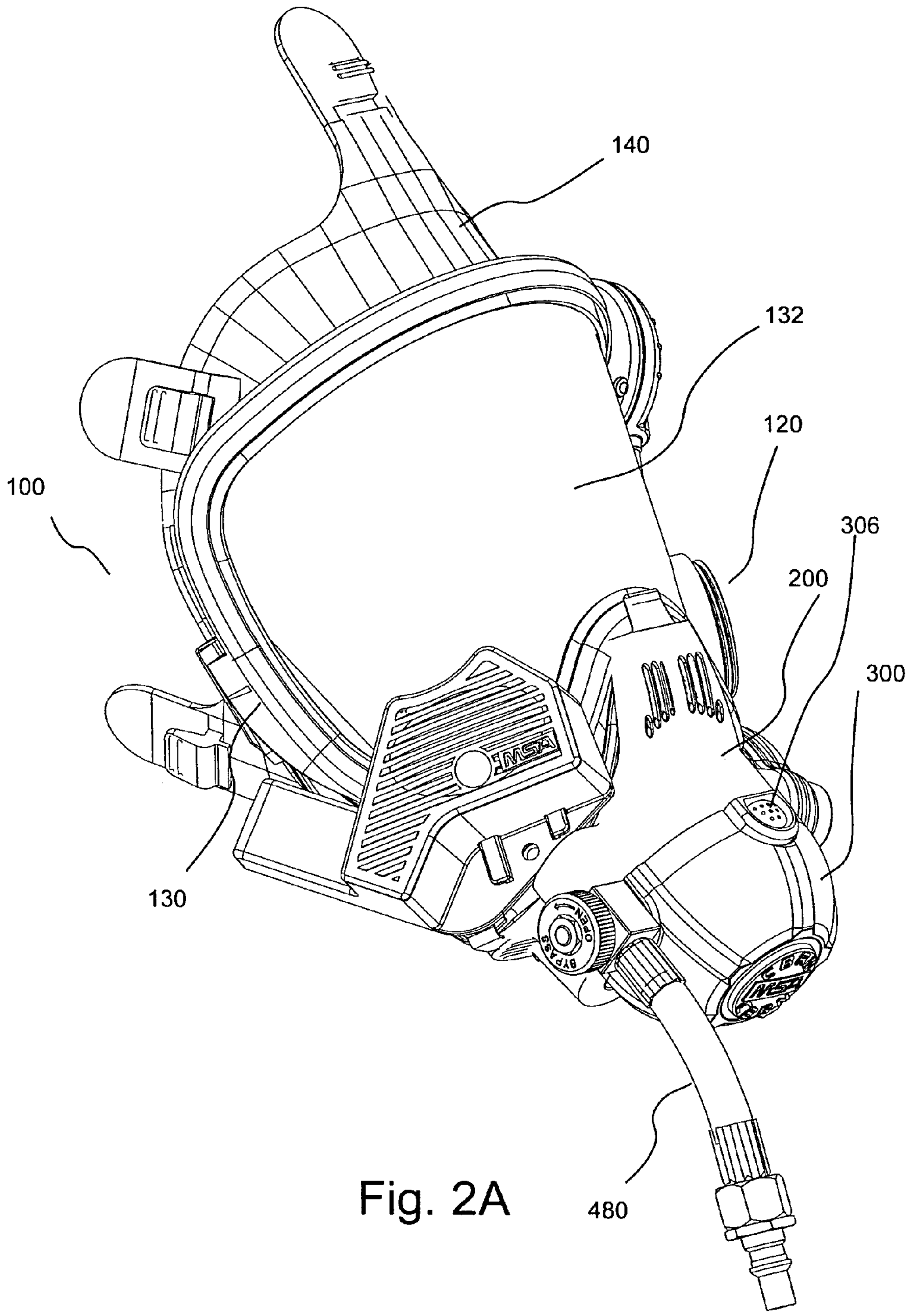
FIG. 2A illustrates an embodiment of a facepiece and a connected regulator assembly of the present invention.
Figure 2B:
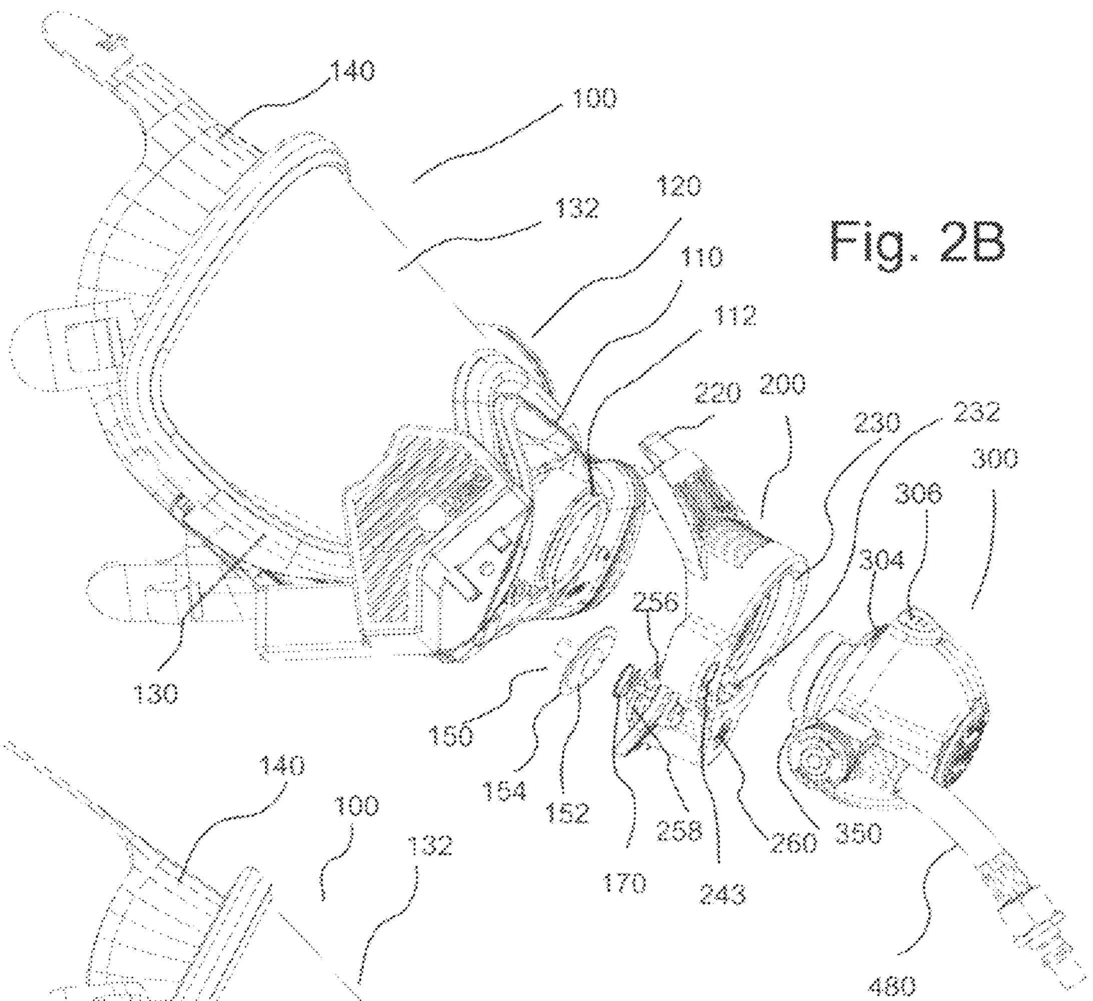
FIG. 2B illustrates an exploded view of the facepiece, the regulator assembly mount of the facepiece and the regulator assembly of FIG. 2A.
Figure 2C:
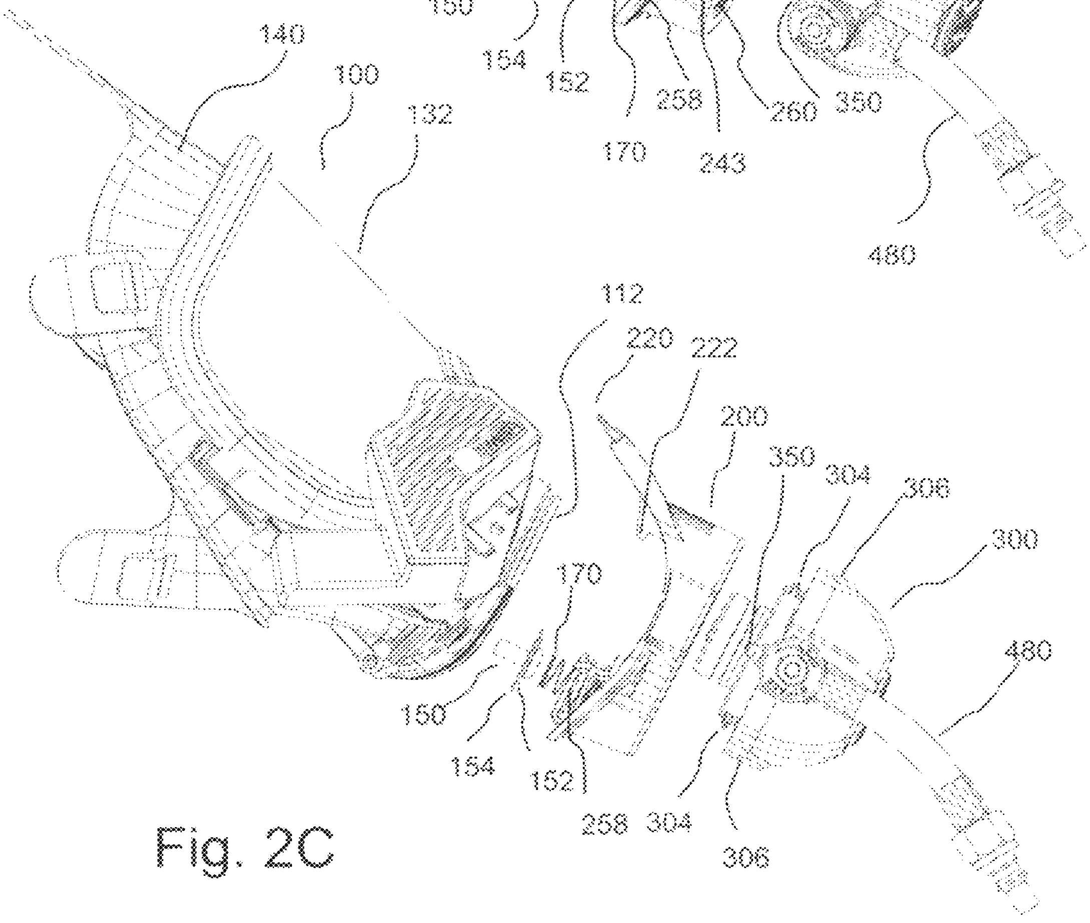
FIG. 2C illustrates another exploded view of the facepiece, the regulator assembly mount and the regulator assembly of FIG. 2A.
Figure 3:
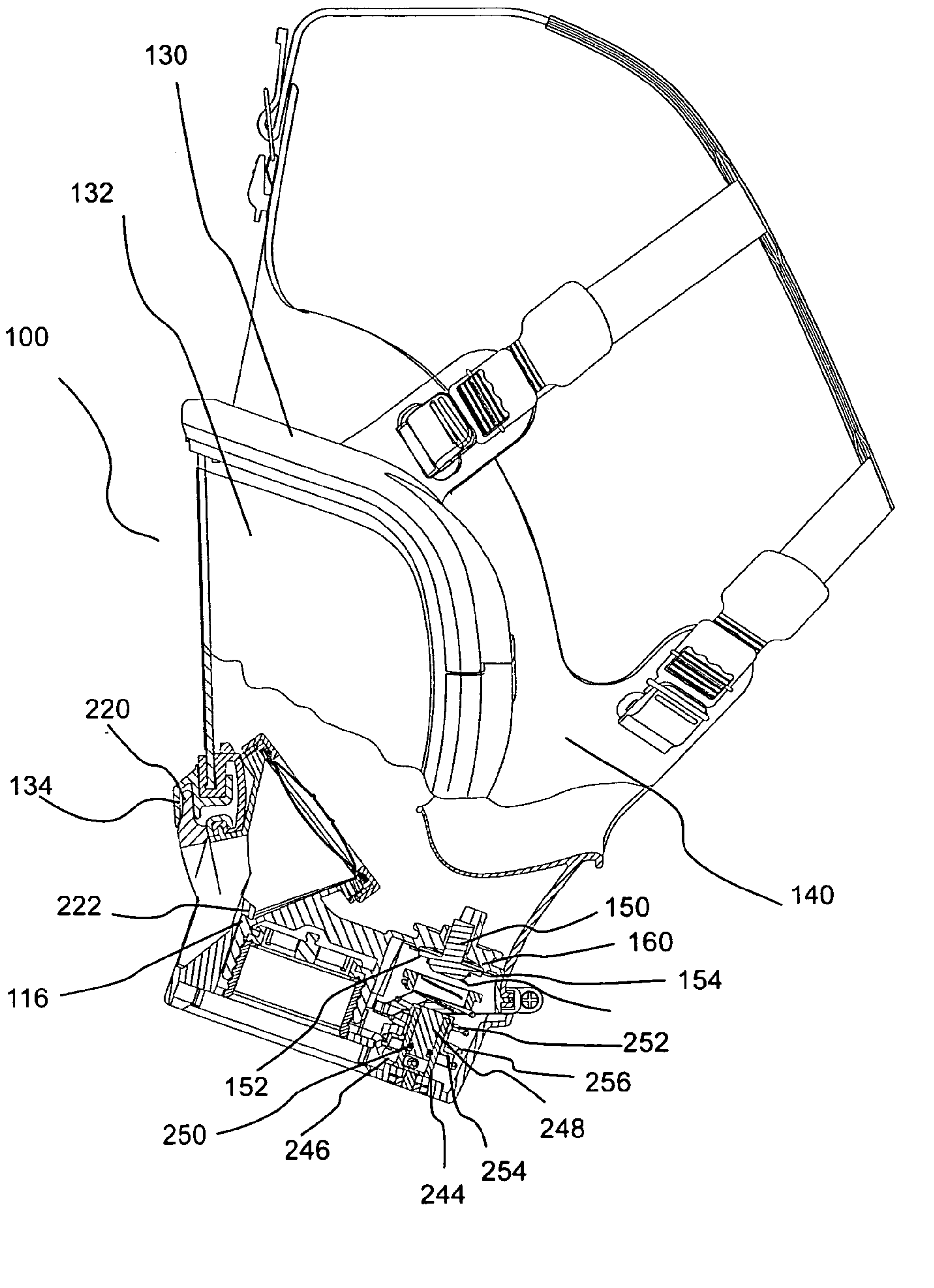
FIG. 3 illustrates a partially cross-sectional, perspective view of the facepiece of FIG. 2A with the regulator assembly mount attached.

FIGS. 1A through 1C illustrate various configurations of a combination breathing system 10 of the present invention. In that regard, FIG. 1A illustrates operation of system 10 of the present invention in an SCBA mode, FIG. 1B illustrates operation of system 10 in an APR mode and FIG. 1C illustrates operation of the system 10 in a PAPR mode. In the illustrated embodiments, combination breathing system 10 includes a facepiece 100. As illustrated for example in FIGS. 2A through 2C, facepiece 100 includes a first port 112 formed in a regulator interface portion 110 of facepiece 100 to place facepiece 100 in fluid connection with a second stage pressure regulator assembly 300 via a mount or mounting interface 200 so that pressurized air can be supplied from a pressurized air tank 400 via hose 480. Pressurized air tank 400 is supported on a harness 450 that is worn by the user of system 10 and includes a valve 470 to provide air to a first stage regulator 475. Facepiece 100 also includes a second port 120 formed in a lens 132 to which a filtering canister 500 (for example, a CBRN/C2 canister available from Mine Safety Appliances Company) can be placed in fluid connection in an APR mode (see FIG. 1B) or to which a PAPR 600 can be attached in an PAPR mode (see FIG. 3). In the SCBA mode (FIG. 1A) a cap 114 can be placed over second port 120. Lens 132 of facepiece 100 is seated in a frame 130. A seal 140 (for example, an elastomeric seal—see FIGS. 1A through 1C) is attached to frame 130 and regulator interface portion 110 and forms a seal with the perimeter of user's face. An elastomeric nose cup 144 (see FIG. 1A) is provided within the interior of facepiece 100. The general operation of a facepiece in a respirator is described, for example, in U.S. patent application Ser. No. 10/143,283, filed May 10, 2002, and published under WO 02/092170.

As further illustrated in FIGS. 2A through 3B, the facepiece further includes an exhalation valve including a valve umbrella 150 that is biased against a valve seat 160. In the illustrated embodiment, valve umbrella 150 includes a generally rigid contact member 152 (for example, a platen or plate) and an elastomeric sealing member 154 attached to a rearward side of contact member 152 and extends beyond the outer edge or perimeter of contact member 152. Unless specifically stated otherwise, as used herein, the terms "rear" or "rearward" refer to a direction toward the user of facepiece 100, and the terms "front" or "forward" refer to a direction away from the user. In the illustrated embodiment, valve umbrella 150 is biased against valve seat 160 via a spring 170.

In the present invention, the force with which sealing member 154 of valve umbrella 150 is biased against valve seat 160 is adjustable to adjust the internal pressure within facepiece 100. In other words, the pressure adjustment mechanism is a mechanism adapted to adjust the force upon valve umbrella 150. In one embodiment, variation in the biasing force on valve umbrella 150 is achieved by varying the working length of spring 170.

Figure 4A:
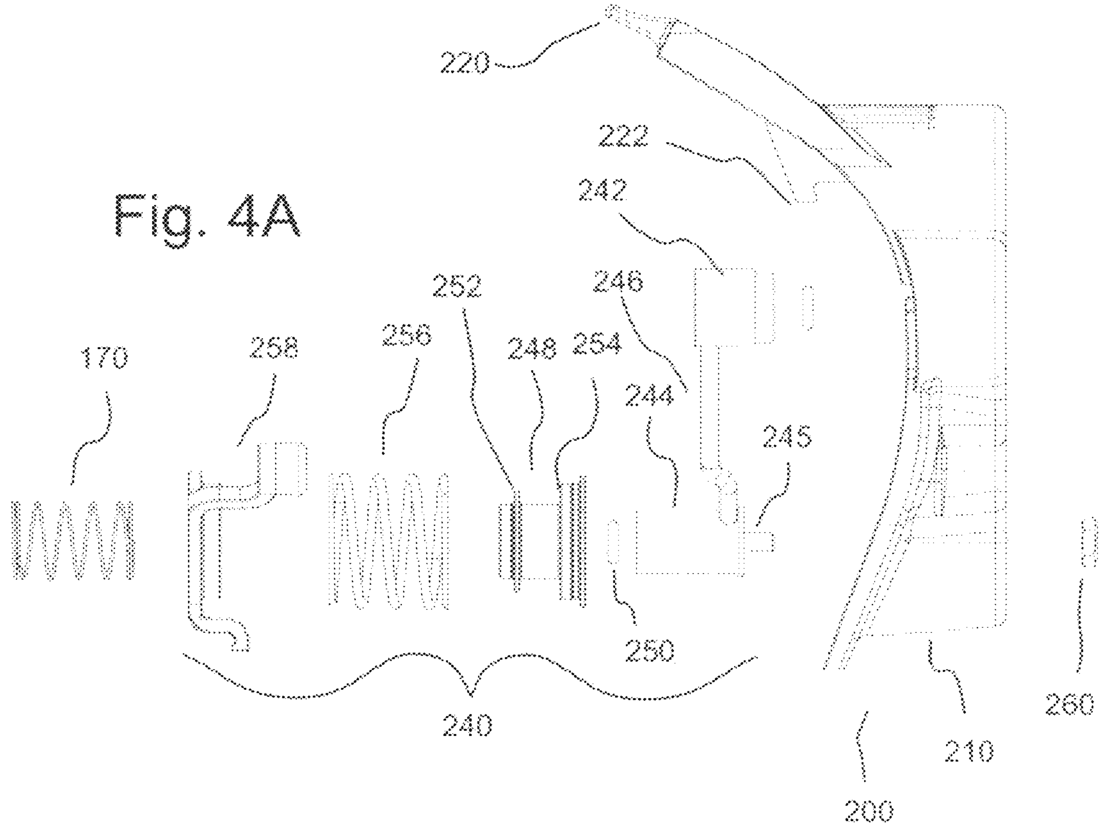
FIG. 4A illustrates a side view of the regulator assembly mount or interface including an exploded side view of an embodiment of a force adjustment assembly that is operable to adjust the force upon the exhalation valve of the facepiece of FIG. 2A to enable operation in a demand mode or in a pressure demand mode, wherein the force adjustment assembly is aligned for seating in the regulator assembly mount.
Figure 4B:
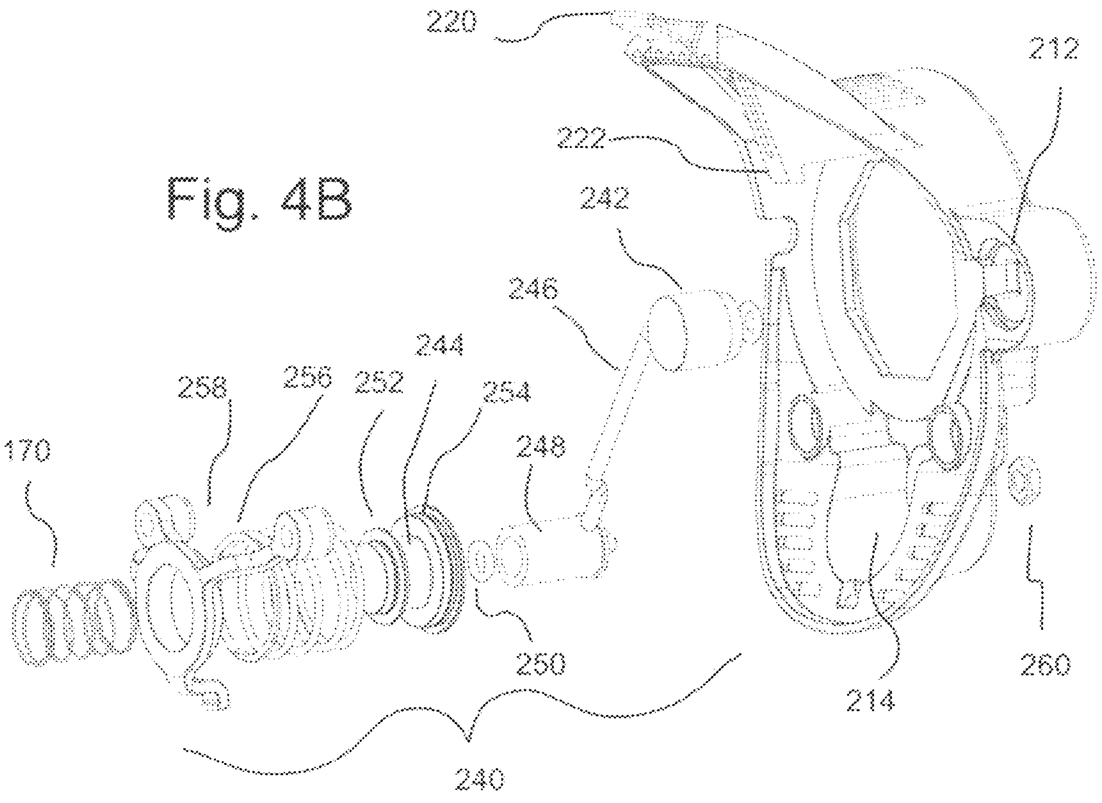
FIG. 4B illustrates a perspective view of the regulator assembly mount including an exploded perspective view of the force adjustment assembly of FIG. 4A, wherein the force adjustment assembly is aligned for seating in the regulator assembly mount.

In that regard, mount interface 200 includes a force adjustment assembly 240 (see, for example, FIGS. 4A and 4B) that is operable to adjust the working length (or the degree of compression) of spring 170. In the illustrated embodiment, pressurized air from first stage regulator 475 is directed from the inlet of second stage regulator assembly 300 and used to adjust the working height of spring 170 and, thereby, the force upon umbrella valve 150 and the pressure within facepiece 100. In that regard, force adjustment assembly 240 includes an air inlet 242 into which pressurized air from first stage regulator 475 is introduced when pressurized air is introduced to pressure regulator assembly 300 (SCBA second stage regulator) via, for example, actuation of actuator or valve 470 in fluid connection with pressurized air tank 400. The pressurized air is introduced into a piston chamber 244 via a conduit or pneumatic tube 246 in fluid connection with air inlet 242. A portion of a piston 248 is slidably positioned within piston chamber 244. A seal is maintained between piston 248 and an inner wall of piston chamber 244 via, for example, an elastomeric seal such as an O-ring 250. Introduction of pressurized air into piston chamber 244 upon activation of air supply actuator valve 470 causes piston 248 to move rearward, toward valve umbrella 150, compressing spring 170, which is in abutting contact with a flange 252 of piston 248, to a first or stressed length corresponding to reduced working length. Once again, the resultant increase of force upon umbrella valve 150 enables the maintenance of in internal pressure within facepiece 100 above ambient pressure.

Upon removal of air pressure from the regulator assembly by deactivation of the air tank actuator valve 470, pressure within piston chamber 244 is decreased and a return spring 256 (which is in abutting contact at a first end thereof with a second flange 254 of piston 248 and is in abutting contact at a second end thereof with a frame member 258 attached to mount 200) causes piston 248 to move forward, away from valve umbrella 150. Spring 170 is thereby allowed to relax or to return to a second length corresponding to an increased working length, decreasing the force upon valve umbrella 150. The reduced force upon valve umbrella 150 allows the exhalation valve umbrella 150 to maintain a seal against exhalation valve seat 160, which enables facepiece 100 to comply with NIOSH breathing resistance criteria established, for example, for APR and PAPR operation modes.

In the embodiment described above, pneumatic pressure is used as a communication link to provide an automatic indication or signal to the pressure adjustment mechanism that the system is pressurized. Moreover, pneumatic pressure is also used to transmit force to valve umbrella 150. Given, the availability of pressurized breathing gas in SCBA or airline systems, several preferred embodiments of the present invention use pneumatic pressure to control a pressure adjustment mechanism without manual intervention. In alternative embodiments, however, other communication links and/or force applicators can be provided to automatically control a pressure adjustment mechanism. For example, a mechanical link (such as a control cable or wire) can be provided between a pressure tank actuator and a pressure adjustment mechanism. A mechanical link can also provide force to, for example, control the position of an abutment member (such as piston 248) to adjust the working length of spring 170 to control the force upon valve umbrella 150. Alternatively, wired or wireless communication systems, as known in the art, can be provided to, for example, actuate an electromechanical actuation system (for example, a solenoid in operative connection with a servo motor) that adjusts the force applied to valve umbrella 150.

Preferably, the adjustment of the exhaust valve opening pressure from demand to a pressure demand mode is made automatically upon opening of valve 470 and adjustment of the exhaust valve opening pressure is made automatically upon closing of valve 470. In that regard, preferably no direct or indirect manual adjustments other than the opening or closing of valve 470 are required to switch the breathing apparatus between a pressure demand mode and a demand mode of operation. As discussed above, available breathing apparatuses that require, for example, manual manipulation of switches (for example, via disconnection/connection of a pressure line) can be prone to failure or contamination resulting from human error or mechanical malfunction.

In the case that pressure is used to communicate the actuation of valve 470 to the pressure adjustment mechanism, pressurized air is preferably supplied to the pressure adjustment mechanism from a point before passing through the second stage regulator (that is, before the pressure is reduced within the second stage regulator). For example, pressurized air can be supplied to the pressure adjustment mechanism from the first stage regulator. The pressure of such air will remain relatively constant and will not be affected by the user's respiration. Pressure of air supplied from an outlet of the second stage regulator can be affected by the user's respiration and may result in fluctuations in the force exerted upon the exhalation valve.

In the illustrated embodiment, air inlet 242 is seated within a first seating 212 formed in a housing 210 of mount 200. Piston chamber 244 and piston 248 are seated within a second seating 214 of housing 210 of mount 200. In the illustrated embodiment, piston chamber 244 includes a threaded extending member 245 which cooperates with a nut 260 to retain piston chamber 244 in secure connection with housing 210.

Mount housing 210 forms a snap fit with facepiece 100 via connectors 220 and 222 which cooperate with a seating 134 formed in frame 130 and a flange 116 formed on regulator interface portion 110, respectively. Mount housing 210 includes an opening 230 about which seatings 232 are positioned. Seatings 232 cooperate with biased (for example, spring-loaded) connectors 304 on regulator assembly 300 to connect regulator assembly 300 to mount 200 and thereby to facepiece 100. Connectors 304 can be moved radially inward via application of a radially inward force to actuator buttons 306 to remove regulator assembly 300 from connection with mount 200.

Figure 5A:
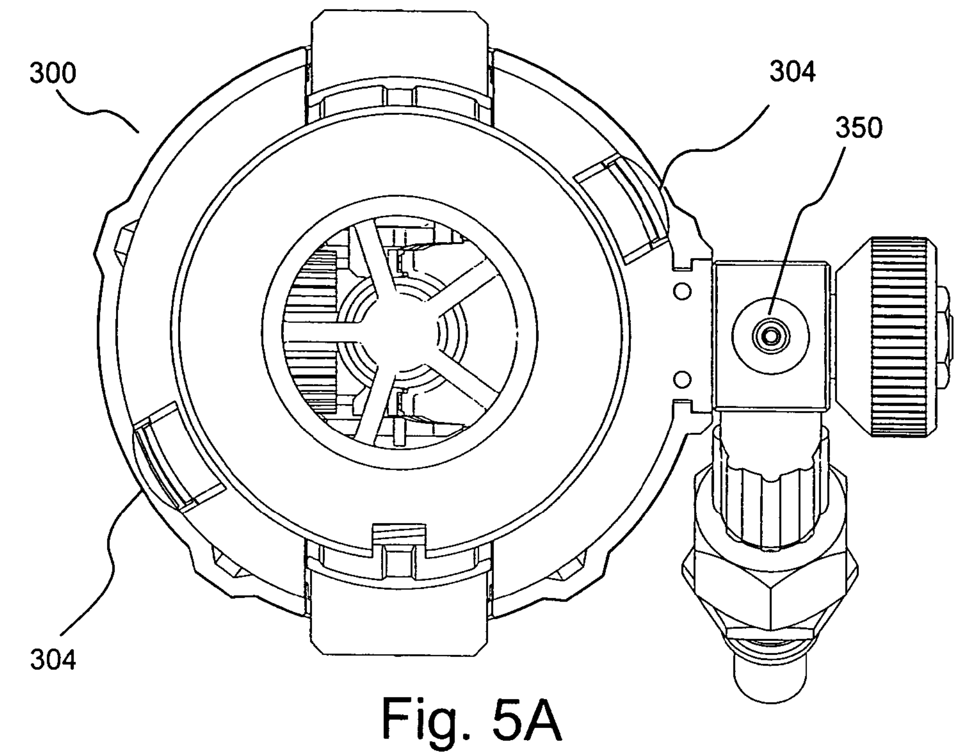
FIG. 5A illustrates a rear view of an embodiment of a regulator assembly for use in connection with the facepiece of the present invention.
Figure 5B:
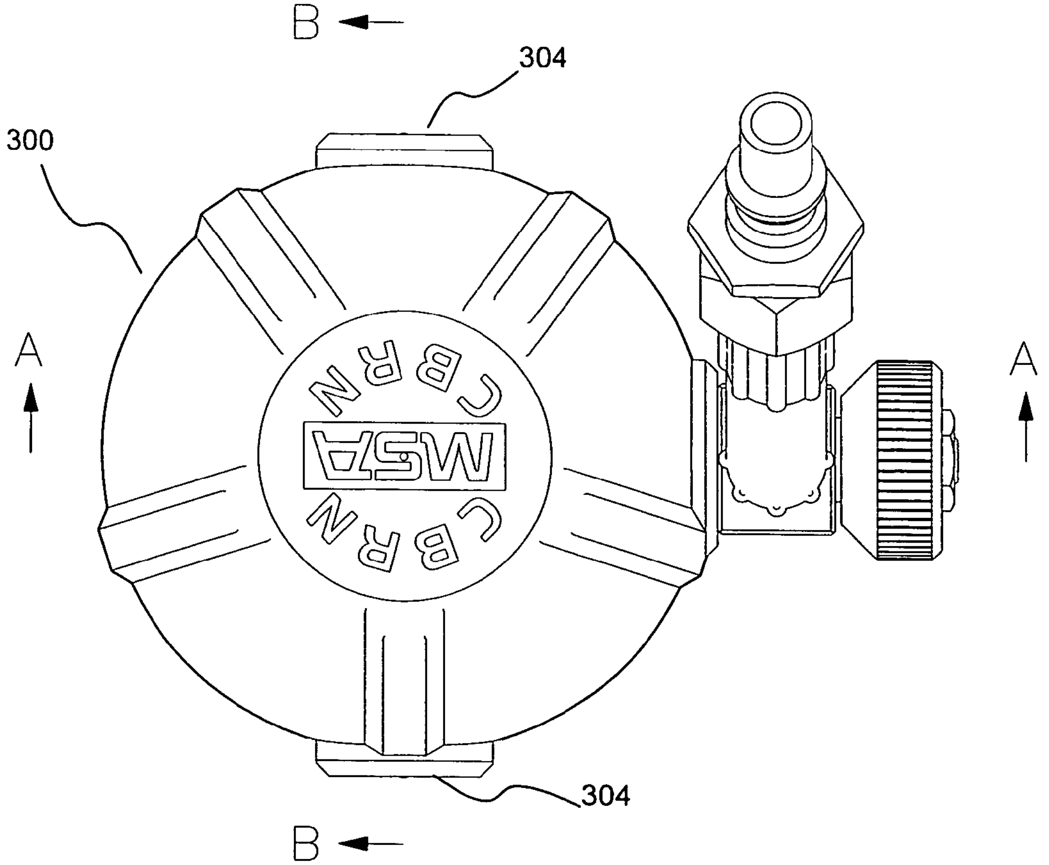
FIG. 5B illustrates a front view of the regulator assembly of FIG. 5A.
Figure 5D:
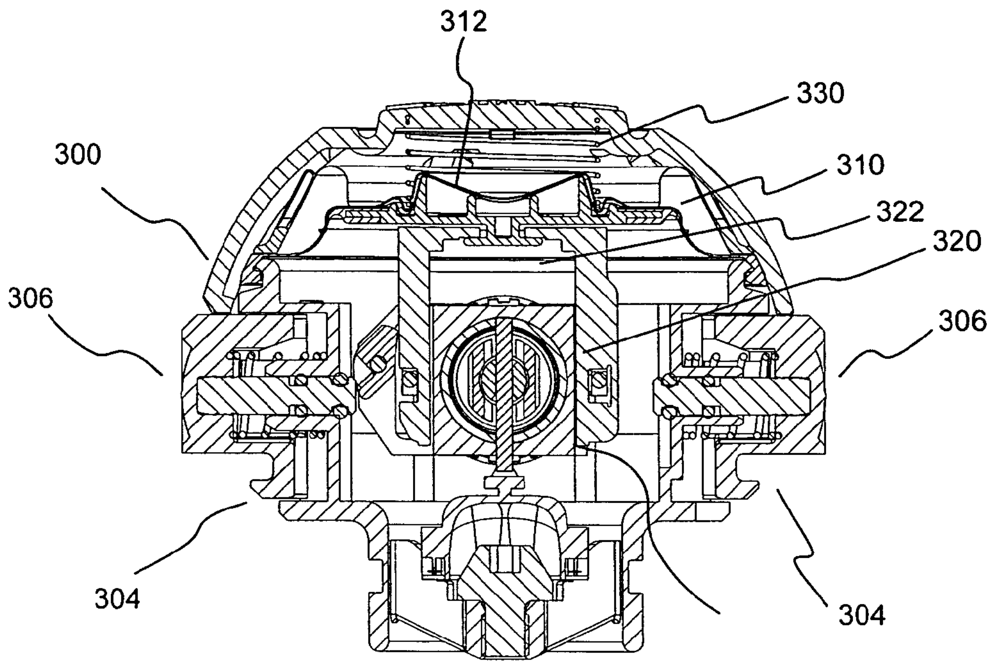
FIG. 5D illustrates a cross sectional view of the regulator assembly of FIG. 5A (Section B-B; see FIG. 5B).
Figure 5C:
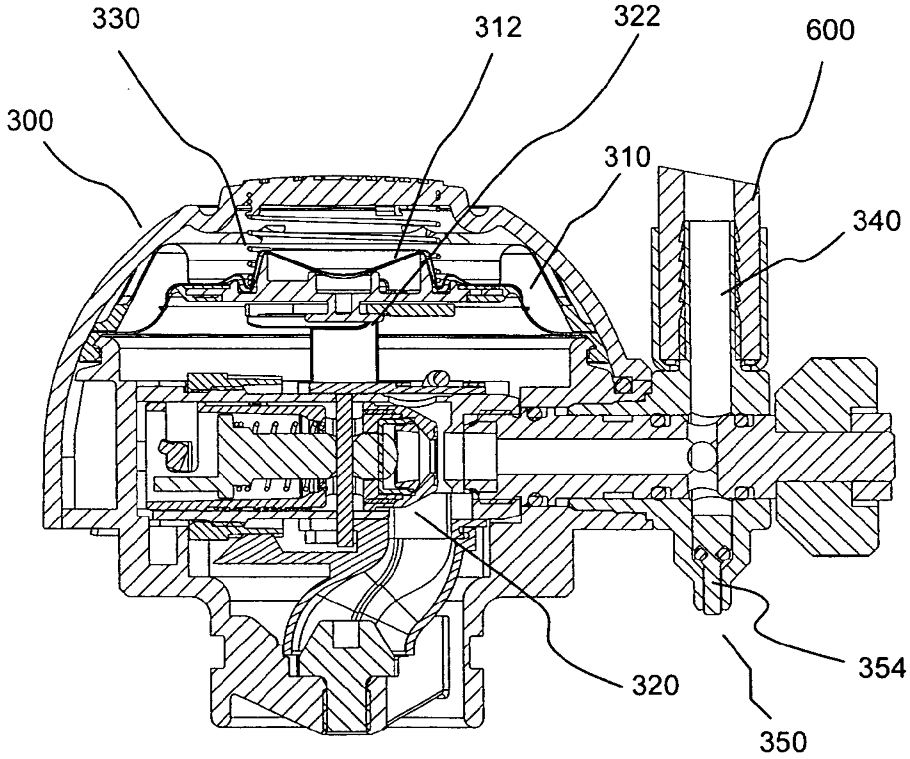
FIG. 5C illustrates a cross sectional view of the regulator assembly of FIG. 5A (Section A-A; see FIG. 5B).

Regulator assembly 300 includes a diaphragm assembly 310 which includes a flexible, elastomeric diaphragm 312 as known in the art. The upper side of elastomeric diaphragm 312 (in the orientation of FIGS. 5C and 5D) is exposed to ambient pressure. On its lower side, elastomeric diaphragm 312 is exposed to the pressure of the interior of facepiece 100 (a positive pressure or a pressure higher than ambient pressure in the case of operation in the pressure demand mode). Elastomeric diaphragm 312 is biased in connection with an actuator 322 of a valve assembly 320 via a spring 330, which also biases valve assembly 320 to assist in ensuring that a positive pressure is maintained within facepiece 310 in a pressure demand mode. Upon inhalation by the user, elastomeric diaphragm 312 is drawn downward from its generally relaxed state and thereby opens valve assembly 330, which is in fluid connection with supply tank 400 of breathing air or breathing gas (via, for example, a connective hose 600 attached to an inlet 340) to allow pressurized air or breathing gas to enter facepiece 100. Upon exhalation, elastomeric diaphragm 312 returns to its rest position, and valve assembly 320 is closed.

Unlike currently available regulator assemblies for use in connection with breathing apparatuses, including SCBAs, regulator assembly 300 includes a port 350 in fluid connection with air inlet 340. Port 350 includes a normally closed check valve 354 in fluid connection therewith. Port 350 is seated within a seating 243 (see FIG. 2B) of air inlet 242 when regulator assembly 300 is attached to mount 200. The seating of port 350 within seating 243 causes valve 354 to open. Upon activation of the breathing apparatus air supply as described above, pressurized air passes from port 350 and into air inlet 242 as described above. The resultant increased forced on valve umbrella 150 via spring 170 allows the facepiece pressure to reach a level above ambient pressure during a complete breathing cycle. As described above, exhalation valve 150 is thus switched automatically from demand mode to pressure demand mode when the breathing apparatus is pressurized upon activation of air supply 400 (via valve 470). Likewise, exhalation valve 150 is switched automatically from pressure demand mode to demand mode when the breathing apparatus air supply 400 is deactivated (via valve 470). Once again, this automatic switching of exhalation modes whenever the breathing apparatus is pressurized or depressurized simplifies the process of switching apparatus modes as compared to currently available combination breathing apparatuses and essentially eliminates the potential of user error.

The foregoing description and accompanying drawings set forth the preferred embodiments of the invention at the present time. Various modifications, additions and alternative designs will, of course, become apparent to those skilled in the art in light of the foregoing teachings without departing from the scope of the invention. The scope of the invention is indicated by the following claims rather than by the foregoing description. All changes and variations that fall within the meaning and range of equivalency of the claims are to be embraced within their scope.

What is claimed is:

1. A breathing system comprising:

a source of pressurized breathing gas;

a regulator assembly comprising an inlet for connection to the source of pressurized breathing gas, an outlet to provide breathing gas to a user and a valve assembly for controlling flow of breathing gas between the inlet and the outlet based at least in part on the respiration of the user;

an actuator via which flow of pressurized breathing gas from the source of pressurized breathing gas to the inlet of the regulator assembly is started when the actuator is placed in a first state and is stopped when the actuator is placed in a second state;

a facepiece comprising a first port adapted to be placed in fluid connection with the outlet of the regulator assembly to introduce pressurized breathing gas into the facepiece, a second port adapted to be connected to an air purifying system; and an exhaust valve through which the user's exhausted breath can exit the facepiece; and a pressure adjustment mechanism in operative connection with the exhaust valve and operable to adjust the internal facepiece pressure required to open the exhaust valve, the pressure adjustment mechanism including a communication link in communicative connection with the actuator such that the exhaust pressure adjustment mechanism sets the internal facepiece pressure required to open the exhaust valve independently of respiration of the user to a first pressure when the actuator is in the first state and the pressure adjustment mechanism sets the internal facepiece pressure required to open the exhaust valve to a second pressure when the actuator is in the second state, the first pressure being higher than the second pressure; wherein the communication link of the pressure adjustment mechanism comprises a pneumatic fluid path providing fluid connection of pressurized breathing gas prior to reduction of pressure of the pressurized breathing gas in the regulator assembly to the pressure adjustment mechanism when the actuator is in the first state and preventing fluid connection of pressurized breathing gas to the pressure adjustment mechanism when the actuator is in the second state.

2. The breathing system of claim 1 wherein the exhaust valve comprises a valve closure member and a valve seating over which the valve closure member is seated to close the exhaust valve, the pressure adjustment mechanism further comprising a force applicating element to place a first force on the valve closure member when the actuator is in the first state and to place a second force on the valve closure member when the actuator is in the second state, the first force being greater than the second force.

3. The breathing system of claim 2 wherein the force applicating element comprises a spring.

4. The breathing system of claim 3 wherein the working length of the spring is adjusted to a first working length by the pressure adjustment mechanism when the actuator is in the first state and the working length of the spring is adjusted to a second working length by the pressure adjustment mechanism when the actuator is in the second state, the first working length being shorter than the second working length.

5. The breathing system of claim 4 wherein the pressure adjustment mechanism further comprises a piston chamber having a piston slidably disposed therein, the spring being in operative connection with the piston, the pneumatic fluid path providing fluid connection between the piston chamber and the regulator assembly inlet, such that the piston is placed in a first position in which it compresses the spring to the first working length when the actuator is in the first state, and the piston is placed in a second position in which the piston allows the spring to relax to the second working length when the actuator is in the second state.

6. The breathing system of claim 5 wherein the piston is biased in the second position such that the piston returns to the second position when the actuator is in the second state.

7. The breathing system of claim 6 wherein the piston is biased in the second position by a return spring.

8. The breathing system of claim 1 wherein the regulator assembly comprises an outlet port in fluid connection with the regulator assembly inlet, the outlet port adapted to make a fluid connection with an inlet port in fluid connection with the pneumatic fluid path when the outlet of the regulator assembly is placed in fluid connection with the first port of the facepiece.

9. The breathing system of claim 8 wherein the outlet port includes a normally closed valve which is opened when the outlet port makes a fluid connection with the inlet port.

10. A facepiece for use in a breathing system comprising:

a first port adapted to be placed in fluid connection with an outlet of a regulator assembly to introduce pressurized breathing gas into the facepiece from a source of pressurized breathing gas;

a second port adapted to be connected to an air purifying system;

an exhaust valve through which the user's exhausted breath can exit the facepiece; and a pressure adjustment mechanism in operative connection with the exhaust valve and operable to adjust the internal facepiece pressure required to open the exhaust valve, the pressure adjustment mechanism including a communication link adapted to be placed in communicative connection with an actuator, the actuator controlling flow of pressurized breathing gas from the source of pressurized breathing gas to the regulator assembly such that flow is started when the actuator is placed in a first state and flow is stopped when the actuator is placed in a second state, the pressure adjustment mechanism setting the internal facepiece pressure required to open the exhaust valve independent of respiration of the user to a first pressure when the actuator is in the first state and the exhaust pressure adjustment mechanism setting the internal facepiece pressure required to open the exhaust valve to a second pressure when the actuator is in second state, the first pressure being higher than the second pressure; wherein the communication link of the pressure adjustment mechanism comprises a pneumatic fluid path providing fluid connection of pressurized breathing gas prior to reduction of pressure of the pressurized breathing gas in the regulator assembly to the pressure adjustment mechanism when the actuator is in the first state and preventing fluid connection of pressurized breathing gas to the pressure adjustment mechanism when the actuator is in the second state.

11. The facepiece of claim 10 wherein the exhaust valve comprises a valve closure member and a valve seating over which the valve closure member is seated to close the exhaust valve, the pressure adjustment mechanism further comprising a force applicating element to place a first force on the valve closure member when the actuator is in the first state and a second force on the valve closure member when the actuator is in the second state, the first force being greater than the second force.

12. The facepiece of claim 11 wherein the force applicating element comprises a spring.

13. The facepiece of claim 12 wherein the working length of the spring is adjusted to a first working length by the pressure adjustment mechanism when the actuator is in the first state and the working length of the spring is adjusted to a second working length by the pressure adjustment mechanism when the actuator is in the second state, the first working length being shorter than the second working length.

14. The facepiece of claim 13 wherein the pressure adjustment mechanism further comprises a piston chamber having a piston slidably disposed therein, the spring being in operative connection with the piston, the pneumatic fluid path providing fluid connection between the piston chamber and the regulator assembly inlet, such that the piston is placed in a first position in which the piston compresses the spring to the first working length when the actuator is in the first state and the piston is placed in the a second position in which the piston allows the spring to relax to the second working length when the actuator is in the second state.

15. The breathing system of claim 14 wherein the piston is biased in the second position such that the piston returns to the second position when the actuator is in the second state.

16. The breathing system of claim 15 wherein the piston is biased in the second position by a return spring.

* * * * *